US012194197B2

United States Patent
Sundaram et al.

(10) Patent No.: US 12,194,197 B2
(45) Date of Patent: Jan. 14, 2025

(54) BORON CARBON NITRIDE (BCN) NANOCOATINGS ON CENTRAL VENOUS CATHETERS INHIBIT BACTERIAL COLONIZATION

(71) Applicant: University of Central Florida Research Foundation, Inc., Orlando, FL (US)

(72) Inventors: Kalpathy B. Sundaram, Orlando, FL (US); Varsha Naga, Oviedo, FL (US); Shraddha Dhanraj Nehate, Orlando, FL (US); Ashwin Kumar Saikumar, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 17/691,587

(22) Filed: Mar. 10, 2022

(65) Prior Publication Data
US 2022/0288281 A1 Sep. 15, 2022

Related U.S. Application Data

(60) Provisional application No. 63/158,999, filed on Mar. 10, 2021.

(51) Int. Cl.
*A61L 29/10* (2006.01)
*A61L 29/04* (2006.01)
*A61L 29/16* (2006.01)

(52) U.S. Cl.
CPC ............. *A61L 29/106* (2013.01); *A61L 29/04* (2013.01); *A61L 29/16* (2013.01); *A61L 2300/404* (2013.01); *A61L 2420/02* (2013.01)

(58) Field of Classification Search
CPC ..... A61F 2/0077; A61L 31/148; C23C 14/28; B23K 26/0821
See application file for complete search history.

(56) References Cited

U.S. PATENT DOCUMENTS

| 5,520,664 A | 5/1996 | Bricault, Jr. et al. |
| 2009/0017318 A1* | 1/2009 | Ruuttu ............... B23K 26/0821 428/457 |
| 2015/0066135 A1* | 3/2015 | Weber ................... A61L 31/148 72/364 |

FOREIGN PATENT DOCUMENTS

| WO | WO-2007096476 A2 * | 8/2007 | ......... A61F 2/30767 |
| WO | 2012177803 A1 | 12/2012 | |
| WO | WO2018/081283 * | 5/2018 | ............. A61L 27/28 |

OTHER PUBLICATIONS

Y. Yao, Y. Ohko, Y. Sekiguchi, A. Fujishima, and Y. Kubota, "Self-sterilization using silicone catheters coated with Ag and TiO2 nanocomposite thin film." Journal of Biomedical Materials Research Part B, 85, 453 (2008).

(Continued)

*Primary Examiner* — Dah-Wei D. Yuan
*Assistant Examiner* — Andrew J Bowman
(74) *Attorney, Agent, or Firm* — Michele L. Lawson; Smith & Hopen, P.A.

(57) ABSTRACT

A novel anti-microbial coating and uses thereof on medical devices are presented. The novel coating is comprised of a layer of boron carbon nitride (BCN) coated onto a medical device such as a catheter. The BCN coating was found to inhibit bacterial growth by at least 80% and reduce biofilm formation by at least 60% on the treated surface of the catheter. This coating can be used to reduce or prevent central line associated bloodstream infections (CLABSI) in (Continued)

patients as well as inhibit bacterial growth and biofilm formation on a variety of medical devices or polymeric surfaces.

3 Claims, 2 Drawing Sheets

(56) References Cited

OTHER PUBLICATIONS

Y. Sekiguchi et al., "Self-sterilizing catheters with titanium dioxide photocatalyst thin films for clean intermittent catheterization: basis and study of clinical use." International Journal of Urology., 14, 426 (2007).

S. Heilman and L. Silva, "Silver and titanium nanoparticles used as coating on polyurethane catheters." Journal of Nano Research: Trans Tech Publ, 47, 17 (2017).

I. Jiménez, R. Torres, I. Caretti, R. Gago, and J. M. Albella, "A review of monolithic and multilayer coatings within the poron-carbon-nitrogen system by ion beam-assisted deposition." J. Mater. Res., 27, 743 (2012).

S. Dou, X. Huang, Z. Ma, J. Wu, and S. Wang, "A simple approach to the synthesis of BCN graphene with high capacitance." Nanotechnology, 26, 045402 (2015).

T. Hirte, R. Feuerfeil, V. Perez-Solorzano, T. Wagner, and M. Scherge, "Influence of composition on the wear properties of boron carbonitride (BCN) coatings deposited by high power impulse magnetron sputtering." Surf. Coat. Technol., 284, 94 (2015).

Chen, Z. and Lu Minghua, "Thionine-coordinated BCN nanosheets for electrochemical enzyme immunoassay of ipocalin-2 on biofunctionalized carbon-fiber microelectrode." Sensors Actuators B, Chemical 273 (2018) 253-259.

Mir, S.H. et al., "Boron-Carbon-Nitride sheet as a novel surface for biological applications: insights from density functional theory." ACS Omega., 4, 3732-3738 (2019).

Naga, V. et al., "Boron Carbon Nitride (BCN) Nano-Coatings of Central Venous Catheters Inhibits Bacterial Colonization." ECS Journal of Solid State Science and Technology, vol. 9, No. 11.

Durmus, N.G. et al., "Fructose-enhanced reduction of bacterial growth on nanorough surfaces." Int. J. Nanomed., 7, 537-545 (2012).

Sukhorukova et al., "Toward bioactive yet antibacterial surfaces." Colloids Surf., B, 135, 158 (2015).

G. Rajakumar et al., "Fungus-mediated biosynthesis and characterization of $TiO_2$ nanoparticles and their activity against pathogenic bacteria." Spectrochim. Acta, Part A, 91, 23 (2012).

Wang, L. et al., "The antimicrobial activity of nanoparticles: present situation and prospects for the future." Int. J. Nanomed., 12, 1227-1249 (2017).

Y. Wu, J. P. Zitelli, K. S. TenHuisen, and X. Yu, "Libera Mr differential response of *Staphylococci* and osteoblasts to varying titanium surface roughness." Biomaterials, 32, 951 (2011).

Feng, G. et al., "Bacterial attachment and biofilm formation on surfaces are reduced by small-diameter nanoscale pores: how small is small enough?" npj Biofilms and Microbiomes., 1, 1-9 (2015).

Hsu, L.C. et al., "Effect of micro-and nanoscale topography on the adhesion of bacterial cells to solid surfaces." Appl. Environ. Microbiol., 79, 2703-2712 (2013).

Friedlander, R.S. et al., "Bacterial flagella explore microscale hummocks and hollows to increase adhesion." Proc. Natl Acad. Sci., Vo. 110, No. 14, 5624-5629 (2013).

Wassil, S.K. et al., "Antimicrobial impregnated catheters in the prevention of catheter-related bloodstream infection in hospitalized patients," J Pediatr Pharmacol Ther, Apr.-Jun. 2007; 12:77-90.

Nehate, S.D. et al., "A review of boron carbon nitride thin films and progress in nanomaterials," Materials Today Advances, 8 (2020) 100106.

Pandit, S. et al., "Antibacterial effect of boron nitride flakes with controlled orientation in polymer composites," The Royal Society of Chemistry, 2019, 9:33454-33459.

Borges, I. et al., "Exposure of smaller and oxidized graphene on polyurethane surface improves its antimicrobial performance," Nanomaterials, 2020, 10, 349.

Gonzalez-Ortiz, D. et al., "Nanostructured boron nitride-based materials: synthesis and applications," Materials Today Advances, 8 (2020) 100107.

Mukheem, A. et al., "Boron nitride doped polyhydroxyalkanoate/chitosan nanocomposite for antibacterial and biological applications," Nanomaterials 2019, 9, 645.

\* cited by examiner

BORON CARBON NITRIDE (BCN) NANOCOATINGS ON CENTRAL VENOUS CATHETERS INHIBIT BACTERIAL COLONIZATION

CROSS REFERENCE TO RELATED APPLICATIONS

This application claims priority to U.S. Provisional Application No. 63/158,999 entitled "Boron Carbon Nitride (BCN) Nanocoatings on Central Venous Catheters Inhibit Bacterial Colonization", filed Mar. 10, 2021, the contents of which are hereby incorporated by reference into this disclosure.

FIELD OF THE INVENTION

This invention relates to antimicrobial coatings for medical devices. More particularly, it relates to an anti-microbial boron carbon nitride nanocoating for medical devices such as catheters.

BACKGROUND OF THE INVENTION

Central line bloodstream infection (CLABSI) remains one of the leading concerns in healthcare facilities with significant contributions to morbidity, costs and mortality. (M. J. Ziegler, D. C. Pellegrini, and N. Safdar, "Attributable mortality of central line associated bloodstream infection: systematic review and meta-analysis." Infection., 43, 29 (2015); C. Sousa, M. Henriques, and R. Oliveira, "Mini-review: antimicrobial central venous catheters-recent advances and strategies." Biofouling., 27, 609 (2011); L. Slobbe, A. el Barzouhi, E. Boersma, and B. J. Rijnders, "Comparison of the roll plate method to the sonication method to diagnose catheter colonization and bacteremia in patients with long-term tunneled catheters: a randomized prospective study." J. Clin. Microbiol., 47, 885 (2009); R. P. Wenzel and M. B. Edmond, "The impact of hospital-acquired bloodstream infections." Emerging Infectious Diseases, 7, 174 (2001); W. R. Jarvis et al., "Nosocomial infection rates in adult and pediatric intensive care units in the United States." The American Journal of Medicine., 91, S185 (1991); M. Tsuboi et al., "Comparison of the epidemiology and microbiology of peripheral line—and central line-associated bloodstream infections." American Journal of Infection Control., 47, 208 (2019)). Annually over 250,000 CLABSIs occur, with an attributable cost per infection estimated at US $34,508-$56,000. (Y. Haddadin and H. Regunath, Central Line Associated Blood Stream Infections (CLABSI). (StatPearls: StatPearls Publishing, Treasure Island (FL)) (2019); J. B. Dimick, R. K. Pelz, R. Consunji, S. M. Swoboda, C. W. Hendrix, and P. A. Lipsett, "Increased resource use associated with catheter-related bloodstream infection in the surgical intensive care unit." Archives of Surgery., 136, 229 (2001)). The annual cost of caring for patients infected with CLABSI lie between $296 million to $2.3 billion. (E. Taylor and T. J. Webster, "Reducing infections through nanotechnology and nanoparticles." Int. J. Nanomed., 6, 1463 (2011)). CLABSI occurs when bacteria or other germs enter the patient's central line and subsequently their bloodstream. CLABSIs are the most common complication of CVCs. However, CVCs are imperative in the delivery of fluids and medications and to monitor patient health.

After insertion, the catheter surfaces are rapidly covered by extracellular host proteins that create an environment conducive to microbial attachment and growth, leading to biofilm formation. (P. N. Danese, "Antibiofilm approaches: prevention of catheter colonization." Chemistry & Biology., 9, 873 (2002)). Leading pathogens responsible for these infections include gram-positive bacteria (such as *Bacillus cereus*) and gram-negative bacteria (such as *Escherichia coli*). (Y. Haddadin and H. Regunath, Central Line Associated Blood Stream Infections (CLABSI). (StatPearls: StatPearls Publishing, Treasure Island (FL)) (2019); D. van Duin et al., "Reduction in central line-associated bloodstream infections in patients with burns." Infection Control & Hospital Epidemiology., 35, 1066 (2014); M. F. Niedner et al., "Epidemiology of central line-associated bloodstream infections in the pediatric intensive care unit." Infection Control & Hospital Epidemiology., 32, 1200 (2011)).

Biofilm protects these pathogens from host's immune defenses and antibiotics, often necessitating removal of the devices to avert life threatening complications. (H. Venter, M. L. Henningsen, and S. L. Begg, "Antimicrobial resistance in healthcare, agriculture and the environment: the biochemistry behind the headlines." Essays in Biochemistry., 61, 1 (2017)). As bacterial biofilms make antibiotic therapies less effective, one of the promising ways of preventing infections is the development of catheter surfaces or materials that work against microbial adhesion. Deposition of metal and metal oxide coatings such as Ag, Ti, $TiO_2$ to inhibit microbial adhesion and reduce biofilm formation on catheters are reported in the literature. (Y. Yao, Y. Ohko, Y. Sekiguchi, A. Fujishima, and Y. Kubota, "Self-sterilization using silicone catheters coated with Ag and $TiO_2$ nanocomposite thin film." Journal of Biomedical Materials Research Part B, 85, 453 (2008); Y. Sekiguchi et al., "Self-sterilizing catheters with titanium dioxide photocatalyst thin films for clean intermittent catheterization: basis and study of clinical use." International Journal of Urology., 14, 426 (2007); S. Heilman and L. Silva, "Silver and titanium nanoparticles used as coating on polyurethane catheters." Journal of Nano Research: Trans Tech Publ, 47, 17 (2017)).

Boron carbon nitride (BCN) compounds have gained attention due to their unique properties such as low dielectric constant, wide bandgap, excellent thermal and mechanical strength, transparency in the optical and UV range. (I. Jiménez, R. Torres, I. Caretti, R. Gago, and J. M. Albella, "A review of monolithic and multilayer coatings within the boron-carbon-nitrogen system by ion beam-assisted deposition." J. Mater. Res., 27, 743 (2012); X. Zhang, "Doping and electrical properties of cubic boron nitride thin films: a critical review." Thin Solid Films, 544, 2 (2013); F. Thevenot, "Boron carbide—a comprehensive review." J. Eur. Ceram. Soc., 6, 205 (1990); A. Prakash, S. D. Nehate, and K. B. Sundaram, "Boron carbon nitride based metal insulator-metal UV detectors for harsh environment applications." Opt. Lett., 41, 4249 (2016)). BCN compounds are known to combine excellent properties of boron carbide ($B_4C$) and boron nitride (BN) with their properties adjustable depending on the composition and structure. As graphite is semi-metallic and h-BN is insulating, BCN, a hybrid between graphite and h-BN, exhibits semiconducting properties. (Y. Li, W. Gao, F. Wang, D. Zhao, Y. Zhang, and H. Yin, "Self-ordered orientation of crystalline hexagonal boron nitride nanodomains embedded in boron carbonitride films for band gap engineering." Coatings., 9, 185 (2019)). BCN has proven to be a multifunctional material finding applications in supercapacitor, UV detectors, anti-wear and protective coatings, and energy storage applications. (Y. Li, W. Gao, F. Wang, D. Zhao, Y. Zhang, and H. Yin, "Self-ordered orientation of crystalline hexagonal boron nitride nanodomains embedded in boron carbonitride films for band gap engineering." Coatings., 9, 185 (2019); S. Wang, F. Ma, H. Jiang, Y. Shao, Y. Wu, and X. Hao, "Band gap-tunable porous Borocarbonitride nanosheets for high energy-density supercapacitors." ACS Applied Materials & Interfaces., 10, 19588 (2018); S. Dou, X. Huang, Z. Ma, J. Wu, and S. Wang, "A simple approach to the synthesis of BCN graphene with high capacitance." Nanotechnology, 26, 045402 (2015); T. Hirte, R. Feuerfeil, V. Perez-Solorzano, T. Wagner, and M. Scherge, "Influence of composition on the wear properties of boron carbonitride (BCN) coatings deposited by high power impulse magnetron sputtering." Surf. Coat. Technol., 284, 94 (2015); J. Caicedo, H. Caicedo, and W. Aperador, "TiN [BCN/BN] n/c-BN system improves the surface properties of machining tools used in industrial applications." The International Journal of Advanced Manufacturing Technology., 77, 819 (2015); H. Tabassum et al., "Large-scale fabrication of BCN nanotube architecture entangled on a three-dimensional carbon skeleton for energy storage." Journal of Materials Chemistry A., 6, 21225 (2018); I. Karbhal, R. R. Devarapalli, J. Debgupta, V. K. Pillai, P. M. Ajayan, and M. V. Shelke, "Facile green synthesis of BCN nanosheets as high-performance electrode material for electrochemical energy storage." Chemistry—A European Journal., 22, 7134 (2016)).

Recently, BCN has been implemented for applications in water purification, nano-biotechnology and nanomedicine field. (Y. Shiraishi, K. Chishiro, S. Tanaka, and T. Hirai, "Photocatalytic dinitrogen reduction with water on boron-doped carbon nitride loaded with nickel phosphide particles." Langmuir, 36, 734 (2020); Z. Chen and M. Lu, "Thionine-coordinated BCN nanosheets for electrochemical enzyme immunoassay of lipocalin-2 on biofunctionalized carbon-fiber microelectrode." Sensors Actuators B, 273, 253 (2018); S. H. Mir, V. K. Yadav, and J. K. Singh, "Boron-Carbon-Nitride sheet as a novel surface for biological applications: insights from density functional theory." ACS Omega., 4, 3732 (2019)). Although BCN has been reported as a novel surface for biological applications, the effectiveness of BCN coatings on inhibiting bacterial growth on medical devices has not been examined.

Various studies have reported coating catheters with titanium dioxide ($TiO_2$) nanoparticles, which has shown some efficacy. $TiO_2$ nanoparticles require UV irradiation for photocatalytic bacterial inhibition to avoid infections. Recent studies have reported titanium (Ti) or its corrosive by-products may cause harmful reactions in humans. $TiO_2$ nanoparticles also have been reported to provoke significant DNA damage in a dose-dependent manner. Further, prior art antibiotic impregnated catheters have failed clinical trials due to the risk of emergence of drug resistant bacteria.

In order to address the shortcomings of the prior art, the inventors investigated the inhibition of bacterial colonies on BCN coated Central Venous Catheters (CVCs) for the first time. BCN nano-coatings inhibit bacterial growth without UV irradiation, unlike $TiO_2$ coated catheters. RF magnetron sputtering technique was used to deposit nano-coatings of BCN and $TiO_2$ on CVCs. BCN coated and uncoated standard catheters were exposed to live cultures of *Escherichia coli* (*E. coli*) and *Bacillus cereus* (*B. cereus*) and colony forming assays were performed. As $TiO_2$ is more commonly used for medical device coatings, the inventors compared bacterial inhibition on BCN films and $TiO_2$ films. Colony forming units (CFUs) for uncoated, $TiO_2$ coated and BCN coated catheters were examined and compared. Accordingly, what is needed is a novel coating for catheters and other medical devices which resists biofilm formation and does not cause harmful reactions in humans.

SUMMARY OF INVENTION

Central line associated bloodstream infections (CLABSI) are commonly caused by bacterial colonization of medical devices such as CVCs and are a leading cause of concern due to increasing hospitalization duration, costs, and morbidity. The inventors evaluated the efficacy of boron carbon nitride (BCN) nano-coatings on CVC for antimicrobial activity. RF magnetron sputtering technique was utilized to deposit nano-coatings of BCN on CVCs. For comparison purposes, RF magnetron sputtered $TiO_2$ nano-coatings were also investigated. Antimicrobial activity of nano-coatings was tested against Gram-positive *Bacillus cereus* and Gram-negative *Escherichia coli* bacterial cells. Nanoparticle coated and uncoated catheter surfaces were studied using FE-SEM (Field Emission Scanning Electron Microscopy) and AFM (Atomic Force Microscopy) to determine if the BCN coated surface characteristics correlated with anti-adhesive effects on bacteria. Biofilm formation on uncoated and BCN coated catheters was quantified using absorbance spectrophotometry.

In an embodiment, a medical device for subcutaneous disposal at least partially within a patient is presented comprising a medical device with a boron carbon nitride (BCN) coating on at least a portion of at least one surface of the medical device. The antimicrobial coating can be a nano-coating that is between about 60-100 nm in thickness and have a surface roughness between about 80-120 nm.

In some embodiments, the medical device may be selected from catheters, implantable biosensors, prosthetic implants, sutures, wound dressings, or surgical drapes. In embodiments where the medical device is a catheter, the antimicrobial coating may be formed on at least a portion of an inner surface of the catheter, on at least a portion of an outer surface of the catheter, or on at least a portion of both the inner and the outer surfaces of the catheter.

Other medical devices contemplated for use with the instant invention include, but are not limited to, certain implantable biosensors, prosthetic implants, sutures, wound dressings, and drapes.

In another embodiment, a method of inhibiting bacterial growth and biofilm formation on a polymeric surface is presented comprising applying a boron carbon nitride (BCN) nano-coating onto at least a portion of the polymeric surface wherein the BCN nano-coating inhibits the bacterial growth and biofilm formation on the polymeric surface.

The BCN nano-coating may be applied to at least one surface of a medical device, such as a catheter. Other medical devices contemplated for use with the instant invention include, but are not limited to, certain implantable biosensors, prosthetic implants, sutures, wound dressings, and drapes such as surgical drapes. The nano-coating can be between about 60-100 nm in thickness and have a surface roughness between about 80-120 nm.

The BCN nano-coating may be applied to the polymeric surface using RF magnetron sputtering with boron carbide having 99.9% purity used as source material. The base pressure of the deposition chamber for the RF magnetron sputtering can be $4 \times 10^{-7}$ Torr. The BCN nano-coating can be applied to the catheter at a fixed pressure of 5 mTorr in presence of $N_2/A$ (0.25) while maintaining total gas flow at 20 sccm. The RF power to the boron carbide source material can be set at 200 W.

Gram-negative, gram-positive, or a combination thereof of the bacterial growth can be inhibited with at least 80% of the bacterial growth on the polymeric surface being inhibited. Biofilm formation on the polymeric surface can be reduced by at least 60%.

In an embodiment, a method of reducing central line associated bloodstream infections (CLABSI) in a patient is presented comprising: providing a central venous catheter coated with a boron carbon nitride (BCN) nano-coating on at least a portion of a surface of the central venous catheter and inserting the BCN coated central venous catheter into the patient wherein the BCN nano-coating inhibits microbial adhesion and biofilm formation on the surface of the central venous catheter to reduce CLABSI in the patient.

The BCN nano-coating can be applied by RF magnetron sputtering wherein the nano-coating is between about 60-100 nm in thickness and has a surface roughness between about 80-120 nm.

BRIEF DESCRIPTION OF THE DRAWINGS

For a fuller understanding of the invention, reference should be made to the following detailed description, taken in connection with the accompanying drawings, in which:

FIG. 1A-E are a series of images depicting FESEM images of (A) UC; (B) $TiO_2C$; and (C) BCN-C. AFM surface topography of (D) UC and (E) BCN-C.

FIG. 2A-H are a series of images depicting the microbial activity on (A) UC; (B) $TiO_2C$; and (C) BCN-C after rolling the catheters onto the surface of nutrient agar plate for *E. coli*. Microbial activity on (D) UC; (E) $TiO_2C$; and (F) BCN-C after rolling the catheters onto the surface of blood agar plates for *B. cereus*. Bar diagram demonstrating inhibition of *E. coli* (G) and *B. cereus* (H) for all the catheters. * represents a statistically significant difference of $p<0.05$ when compared to the control sample which is U-C. ** represents $p<0.01$.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that there are other embodiments by which the invention may be practiced. It is to be understood that other embodiments may be utilized and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

As used in the specification and claims, the singular form "a," "an" and "the" include plural references unless the context clearly dictates otherwise.

As used herein, the term "comprising" is intended to mean that the products, systems and methods include the referenced components or steps, but not excluding others. "Consisting essentially of" when used to define products, systems and methods, shall mean excluding other components or steps of any essential significance. "Consisting of" shall mean excluding more than trace elements of other components or steps.

All numerical designations, including ranges, are approximations which are varied up or down by increments of 1.0 or 0.1, as appropriate. It is to be understood, even if it is not always explicitly stated that all numerical designations are preceded by the term "about".

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

The term "about" or "approximately" as used herein refers to being within an acceptable error range for the particular value as determined by one of ordinary skill in the art, which will depend in part on how the value is measured or determined. As used herein the term "about" refers to ±10% of the numerical.

"Infection" as used herein refers to the invasion of one or more microorganisms such as bacteria, viruses, fungi, yeast or parasites in the body of a patient in which they are not normally present.

"Prevention" or "preventing" as used herein refers to any of: halting the effects of infection or pain, reducing the effects of infection or pain, reducing the incidence of infection or pain, reducing the development of infection or pain, delaying the onset of symptoms of infection or pain, increasing the time to onset of symptoms of infection or pain, and reducing the risk of development of infection or pain.

"Antimicrobial" or "antimicrobial agent" as used herein refers to natural or synthetic compositions capable of killing or inhibiting the growth of microorganisms including, but not limited to, bacteria, fungi, viruses, protozoa and parasites. Antimicrobials used herein include antibiotics, antivirals, antifungals, antiprotozoals, and antiparasitics. Exemplary antimicrobials that may be used herein include, but are not limited to, boron carbon nitride.

"Biofilm" as used herein refers to a layer of microorganisms, encased in a matrix, which forms on a biotic or abiotic surface. In many cases, the biofilm is formed from a community of bacteria enclosed in an exopolysaccharide matrix. A biofilm is usually resistant to antibiotics. The biofilm may be monomicrobial or polymicrobial.

"Patient" is used to describe an animal, preferably a mammal, more preferably a human, to whom treatment is administered, including prophylactic treatment with the compositions of the present invention.

"Medical device" as used herein refers to any apparatus, implant, appliance, or machine capable of being used with a patient for a medical purpose. Exemplary medical devices for use with the instant invention include, but are not limited to, catheters, certain implantable biosensors, prosthetic implants, sutures, wound dressings, and drapes. In some embodiments, the medical device is capable of being at least partially implanted in a patient's body. In other embodiments, the medical device is fully implanted in the patient, e.g. prosthetic joints of the hips, knees, shoulders, elbows, ankles, and wrists.

In some embodiments, the medical device is a transcutaneous medical device which passes through the skin so that at least a portion of the device resides inside the body of the patient for a considerable amount of time (generally greater than 24 hours) during the course of function of the device. Such transcutaneous medical devices include, but are not limited to, catheters, such as central venous catheters, peripheral venous catheters, Swan-Gaus pulmonary catheters, peritoneal dialysis catheters, and hemodialysis catheters; pins, such as temporary orthopedic pins; transvenous pacemaker leads; and implants, such as central nervous system implants. Such transcutaneous medical devices may have a portion of the device residing within the body of the patient while another portion of the device resides outside of the body of the patient. In some cases, the transcutaneous device may be a long-term transcutaneous device, such as catheters, certain biosensors, and infusion devices, which require the patient to endure extended cutaneous wounds that can be difficult to manage infection and inflammation.

"Catheter" as used herein refers to a hollow tube formed from a biocompatible material for insertion into body cavities to drain fluids, inject fluids or distend body passages. The hollow tube may be flexible or rigid depending on the use. The term "catheter" includes, but is not limited to, a chest tube (intercostal drain, thoracic catheter, thoracostomy tube), central line, intravenous catheter, Blake drain, pigtail catheter, pleural catheter, Foley catheter, and hemodialysis catheters. In some embodiments, the catheter is made of a polymeric material.

"Polymeric" or "polymer" as used herein refers to a relatively high molecular weight organic compound, natural or synthetic, whose structure can be represented by a repeated small unit, the monomer. Synthetic polymers are typically formed by addition or condensation polymerization of monomers. A polymer comprised of two or more different monomers is a copolymer.

Boron carbon nitride ($B_xC_yN_z$) compounds are known to combine excellent properties of boron carbide ($B_4C$) and boron nitride (BN). The properties are tunable depending on the composition and structure. While graphite is semi-metallic and BN is insulating, hybrid $B_xC_yN_z$ compounds between graphite and BN exhibit semiconducting properties which makes them different from pure BN compounds. As the elemental composition varies between carbon and BN, the properties of $B_xC_yN_z$ compounds change to allow flexibility of tuning compounds for desired requirements.

Here, the inventors deposited BCN films using a single-step deposition technique with a separate $B_4C$ target. By controlling the deposition parameters, BCN film elemental composition can be directed effectively to yield a film with bacterial inhibition properties and high carbon content. While the invention references a single-step deposition technique for depositing the film on a substrate, this is meant to be exemplary and not meant to limit the invention in any way. Any deposition technique capable of depositing a BCN nano-coating, having the requisite thickness and surface roughness parameters as described herein, on a substrate, is contemplated. Examples of deposition techniques include, but are not limited to, chemical vapor deposition (CVD), magnetron sputtering, pulsed laser deposition (PLD), and ion beam-assisted deposition (IBAD). While the examples describe deposition of the BCN coating on a polymeric surface, these examples are meant to be illustrative and not construed in a limiting way. Other surfaces are contemplated for use with the antimicrobial BCN coatings.

The inventors tested their BCN nano-coatings against prior art $TiO_2$ coated catheters. Antimicrobial activity of nano-coatings was tested against Gram-positive *Bacillus cereus* and Gram-negative *Escherichia coli* bacterial cells. BCN nano-coatings performed better to inhibit bacteria growth on catheters compared to $TiO_2$ coated catheters. Specifically, $TiO_2$ coated catheter reduced bacterial colony-forming units by 19% for *E. coli* as compared to 81% for BCN coated catheter. The bacterial colony-forming reduction of *B. Cereus* was 19% for $TiO_2$ coated catheters as against 97% for BCN coated catheters.

The BCN nano-coating is described in the Examples as being between about 80-90 nm in thickness. This range is exemplary and is not meant to be limiting in any way. Exemplary ranges include, but are not limited to, 60 nm to 100 nm; 70 nm to 100 nm; 80 nm to 100 nm; 60 nm to 90 nm; 70 nm to 90 nm; and all individual values and subranges in between.

The BCN nano-coating is described in the Examples as being about 90 nm in average surface roughness. This value is exemplary and is not meant to be limiting in any way. Surface roughness above 80 nm is contemplated, with an upper threshold of 120 nm, including all values and subranges in between.

It is understood and herein contemplated that the BCN coating does not have to be coated only onto a catheter, but can be coated onto the surface of any medical device designed to be implanted, or partially implanted, into a patient including, but not limited to, prosthetic implants. The BCN coating can also be used to coat any polymeric surface of a device or apparatus desiring antimicrobial properties. With respect to catheters, the coating is efficient on any type of catheter including, but not limited to, central line, intravenous, urinary, etc. In addition, the coating may be applied onto items used to treat a wound including, but not limited to, adhesive bandages, wound dressings, surgical drapes, and sutures.

The following non-limiting examples illustrate exemplary systems and components thereof in accordance with various embodiments of the disclosure. The examples are merely illustrative and are not intended to limit the disclosure in any way.

Example 1—Antibacterial Coating on Catheter

In an embodiment, the inventors have developed an antimicrobial coating for a catheter thus producing an antimicrobial catheter. The antimicrobial coating is comprised of a boron carbon nitride (BCN) coating. This BCN coating successfully inhibited at least 80% bacterial growth on the treated surface of the catheter and was efficient at inhibiting both Gram-positive and Gram-negative bacteria. In addition, the BCN coating successfully inhibited biofilm formation on the catheter at least 60%. These results far outperformed catheters coated with $TiO_2$. As used herein, uncoated catheters, $TiO_2$ nano-coating catheters and BCN nano-coating catheters will be referred as U-C, $TiO_2$—C and BCN-C, respectively.

Results

Surface Characterization of Nano-Coatings

Figure 1A:
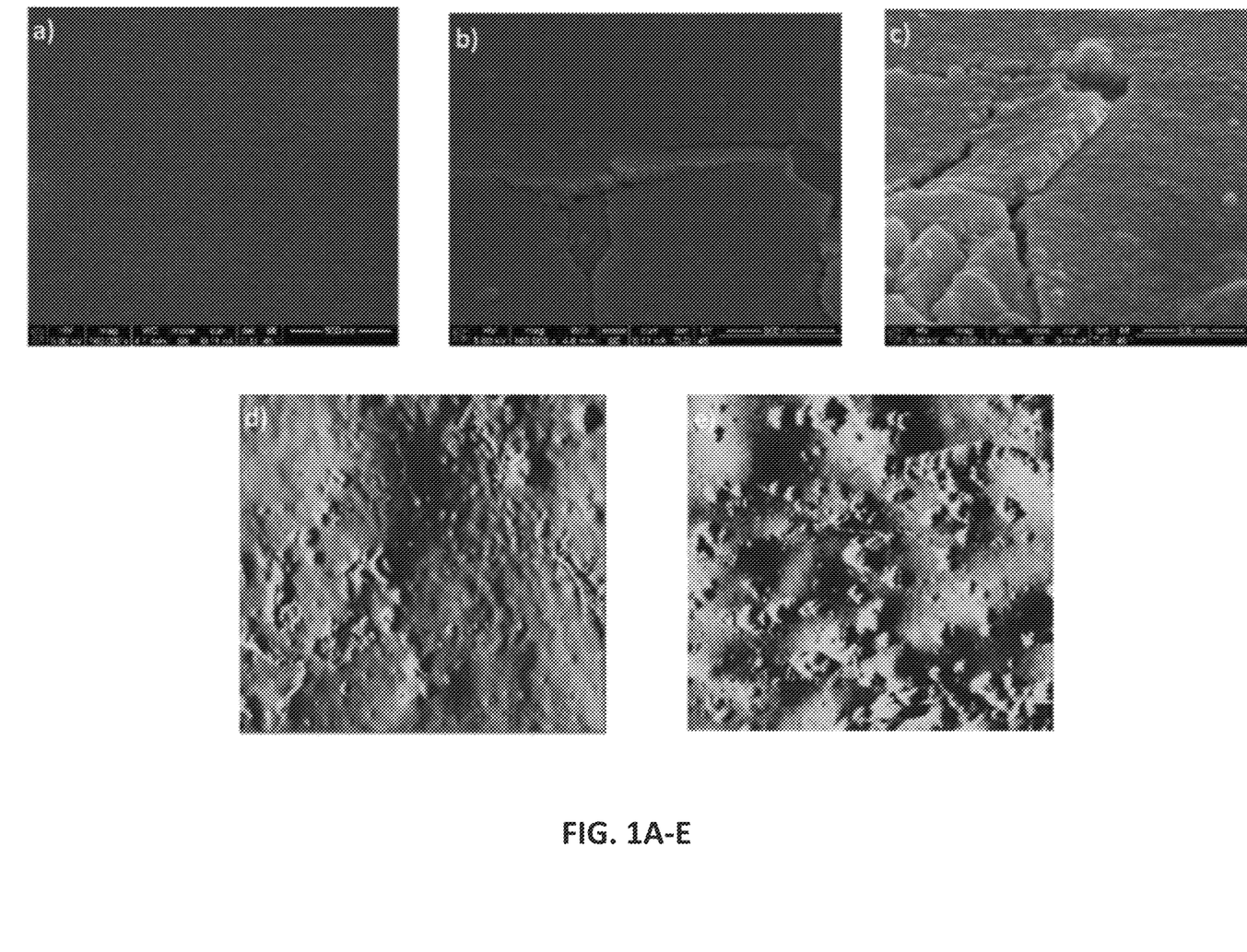

The film thickness of BCN and $TiO_2$ coatings ranged between 80-90 nm. Surface morphology of the deposited nano-coatings was determined before the evaluation of antimicrobial activity. FIGS. 1A-1C shows the FESEM pictures of U-C, $TiO_2$—C and BCN-C surfaces, respectively.

U-C exhibited smooth surface morphology. Compared to U-C and $TiO_2$—C, BCN-C surface displayed significant nano-protrusions. Given the BCN-C surface differences observed in FESEM, noncontact AFM characterization was performed to evaluate surface roughness of U-C and BCN-C. FIGS. 1D and 1E show the AFM scans of U-C and BCN-C conducted on catheter surfaces. The average surface roughness of U-C was recorded to be 41.7 nm, whereas BCN-C exhibited average surface roughness of 90.7 nm. In separate 10 $\mu m^2$ surface scans, BCN-C exhibited 15-fold higher peak gradient difference as compared to U-C.

Inhibitory Effects of Bacterial Growth on BCN-C

Table I shows the CFUs of *E. coli* bacteria for UC, $TiO_2$—C and BCN-C recorded after 24 h of incubation. Results of three individual experiments are displayed. The uncoated catheters demonstrated the highest number of bacterial CFUs. $TiO_2$—C demonstrated slightly lower CFUs compared to U-C, however, this difference was not significant implying that $TiO_2$ coating did not inhibit colonization by *E. coli*. BCN-C demonstrated 81.14% reduction in *E. coli* CFUs when compared to the U-C, thus confirming the anti-bacterial activity of BCN coatings.

TABLE 1

CFUs of *E. coli* on UC, $TiO_2$—C and BCN-C.

| | Number of CFUs | | | Average % Decrease in CFU | |
|---|---|---|---|---|---|
| Trial | U-C | $TiO_2$—C | BCN-C | $TiO_2$—C | BCN-C |
| 1 | 29 | 24 | 3 | 19.19 | 81.14 |
| 2 | 26 | 20 | 4 | | |
| 3 | 34 | 28 | 10 | | |
| Average | 29.7 | 24.0 | 5.6 | | |

Table II shows the CFUs of *B. cereus* bacteria recorded for U-C, $TiO_2$—C and BCN-C after incubation. Experimental results of three individual experiments are displayed. It can be seen that the average CFUs of U-C was 104.3 which reduced to 84.3 for $TiO_2$—C, and 3 for BCN-C. Although $TiO_2$—C exhibited only 19.17% decrease in bacterial colonies, BCN-C exhibited an excellent 97.12% decrease in *B. cereus* bacterial colonization. This reduction observed in bacterial activity of *E. coli* and *B. cereus* on BCN-C could be attributed to high surface roughness of BCN-C. The correlation between bacterial adhesion and surface roughness has been investigated. (G. Feng, Y. Cheng, S.-Y. Wang, D. A. Borca-Tasciuc, R. W. Worobo, and C. I. Moraru, "Bacterial attachment and biofilm formation on surfaces are reduced by small-diameter nanoscale pores: how small is small enough?" npj Biofilms and Microbiomes., 1, 1 (2015)). A surface under magnification appears as a series of peaks and valleys with varying height and spacing. Surface roughness is determined by the height variation between these peaks and valleys on the surface of interest. It is commonly accepted that nanorough surfaces have a lower probability of bacterial adhesion when compared to smooth surfaces. (N. G. Durmus, E. N. Taylor, F. Inci, K. M. Kummer, K. M. Tarquinio, and T. J. Webster, "Fructose-enhanced reduction of bacterial growth on nanorough surfaces." Int. J. Nanomed., 7, 537 (2012)). Similar trend in surface roughness of coatings and bacterial adhesion has been reported. (I. Sukhorukova et al., "Toward bioactive yet antibacterial surfaces." Colloids Surf., B, 135, 158 (2015); G. Rajakumar et al., "Fungus-mediated biosynthesis and characterization of $TiO_2$ nanoparticles and their activity against pathogenic bacteria." Spectrochim. Acta, Part A, 91, 23 (2012); L. Wang, C. Hu, and L. Shao, "The antimicrobial activity of nanoparticles: present situation and prospects for the future." Int. J. Nanomed., 12, 1227 (2017); Y. Wu, J. P. Zitelli, K. S. TenHuisen, and X. Yu, "Libera Mr differential response of Staphylococci and osteoblasts to varying titanium surface roughness." Biomaterials, 32, 951 (2011)). PGP-22

TABLE 2

CFUs of *B. cereus* on U-C, $TiO_2$—C and BCN-C.

| | Number of CFUs | | | Average % decrease in CFUs | |
|---|---|---|---|---|---|
| Trial | U-C | $TiO_2$—C | BCN-C | $TiO_2$—C | BCN-C |
| 1 | 96 | 67 | 1 | 19.17 | 97.12 |
| 2 | 101 | 88 | 2 | | |
| 3 | 116 | 98 | 6 | | |
| Average | 104.3 | 84.3 | 3.0 | | |

Figure 2A:
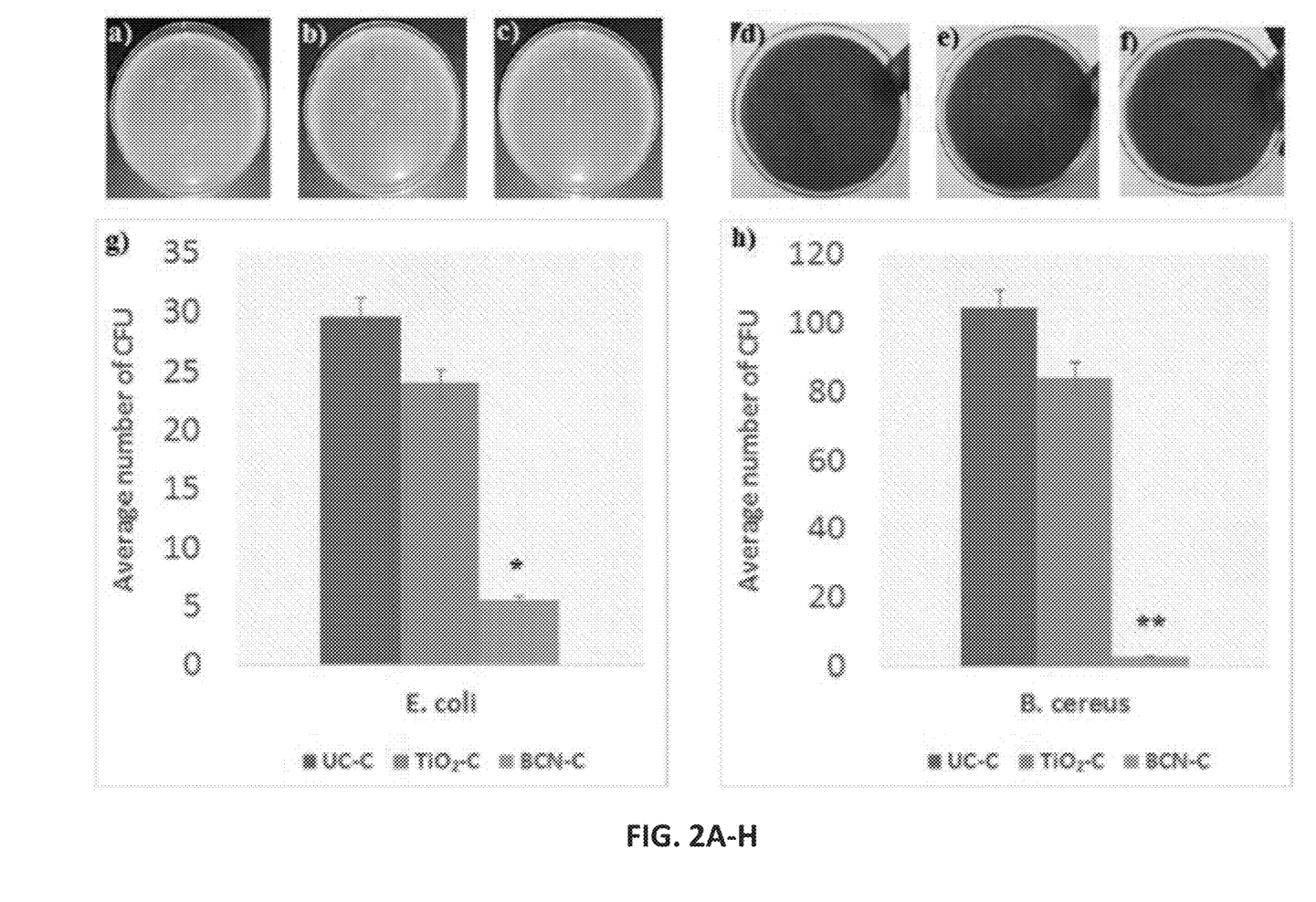

FIGS. 2A-2C shows *E. coli* bacterial colonies after rolling the catheters onto the surface of nutrient agar plates. FIGS. 2D-2F shows *B. cereus* bacterial colonies after rolling the catheters onto the surface of blood agar plates. FIGS. 2G and 2H shows the average number of CFUs plotted for the three types of catheters examined. Reduction in bacterial CFUs on BCN-C was statistically significant with p value of 0.0008 for *E. coli*. Similarly, BCN-C displayed excellent reduction in bacterial CFUs for *B. cereus* with highly significant p value of 0.00004.

Biofilm Formation

BCN-C exhibited excellent bacterial inhibition when compared to $TiO_2$. To further study the strong inhibition of *E. coli* and *B. cereus* on BCN nanocoated catheters, biofilm formation was quantified using absorbance spectrophotometry. Table III displays the optical density values of the stained biofilms formed by *E. coli* and *B. cereus*. BCN-C reduced biofilm formation by 62.13% for *E. coli* and 75.52% for *B. cereus*. This biofilm inhibitory property of BCN nano-coatings can be attributed to the surface roughness which impacts the surface topography. As BCN-C surface topographic features are in nanometric range, which is much smaller than the microbial cell size, there is a significant decrease in the contact area between bacterial cell and the nanocoated surface. This may influence the activation of bacterial adhesion genes and genes that secrete extracellular matrix, thereby affecting cell attachment and subsequent biofilm formation on BCN-C.

TABLE 3

Optical density (OD) of E. coli and B. cereus of BCN-C in comparison with U-C.

| Trial | OD of E. coli stained catheters U-C | OD of E. coli stained catheters BCN-C | % decrease in E. coli OD | OD of B. cereus stained catheters U-C | OD of B. cereus stained catheters BCN-C | % decrease in B. cereus OD |
|---|---|---|---|---|---|---|
| 1 | 0.4868 | 0.1839 | 62.13 | 0.6398 | 0.1451 | 75.52 |
| 2 | 0.5006 | 0.1613 | | 0.5308 | 0.1271 | |
| 3 | 0.4680 | 0.2070 | | 0.5964 | 0.1589 | |
| Average | 0.4851 | 0.1837 | | 0.5880 | 0.1439 | |

There is increasing evidence that bacterial adhesion and subsequent biofilm formation are greatly impacted by the surface topography. (G. Feng, Y. Cheng, S.-Y. Wang, D. A. Borca-Tasciuc, R. W. Worobo, and C. I. Moraru, "Bacterial attachment and biofilm formation on surfaces are reduced by small-diameter nanoscale pores: how small is small enough?" npj Biofilms and Microbiomes., 1, 1 (2015); L. C. Hsu, J. Fang, D. A. Borca-Tasciuc, R. W. Worobo, and C. I. Moraru, "Effect of micro- and nanoscale topography on the adhesion of bacterial cells to solid surfaces." Appl. Environ. Microbiol., 79, 2703 (2013); R. S. Friedlander, H. Vlamakis, P. Kim, M. Khan, R. Kolter, and J. Aizenberg, "Bacterial flagella explore microscale hummocks and hollows to increase adhesion." Proc. Natl Acad. Sci., 110, 5624 (2013)).

These results indicate that BCN nano-coatings demonstrate antibiofilm activity which reduces colonization rates on CVCs. This reduction in colonization can also reduce the incidence of CLABSIs, which in turn reduces antibiotic use and deters the development of antibiotic resistant organisms.

Materials and Methods

BCN and $TiO_2$ Nano-Coatings

Nano-coatings were deposited using RF magnetron sputtering technique. This technique directs highly energetic Ar ions to bombard the surface of high purity source material to be deposited, which causes the ejection of source target atoms by momentum transfer. Since the sputtering is performed in high vacuum ambiance, ejected source material atoms are deposited onto the substrate surface, subsequently forming the required thin film. The source material was boron carbide ($B_4C$) target and the deposition was performed in presence of inert argon and reactive nitrogen gas.

CVCs were cut into 7 cm long segments and were coated with either BCN or $TiO_2$ respectively using an AJA ultra-high vacuum 3-gun sputtering system. For BCN films, the source material was a $B_4C$ target with 99.9% purity. The base pressure of deposition chamber was $4 \times 10^{-7}$ Torr. BCN nano-coatings were deposited at a fixed pressure of 5 mTorr in presence of $N_2/Ar$ (0.25) while maintaining the total gas flow at 20 sccm. RF power to the $B_4C$ target was set at 200 W. For $TiO_2$ nano-coatings on CVCs, 99.9% purity Ti target was used as source material in presence of $O_2/Ar$ (0.25) gas. The working pressure was set as 10 mTorr at 50 W RF power to the Ti target. The depositions were performed at room temperature for both BCN and $TiO_2$ nano-coatings.

Surface Characterization of the Nano-Coatings

Thickness of the BCN and $TiO_2$ coatings was measured using Dektak 150 stylus profilometer (Veeco). After coating the CVCs with BCN and $TiO_2$ layers, field emission scanning electron microscopy (FESEM) and atomic force microscopy (AFM) were used for surface characterization.

The FEI NOVA 430 SEM was used to observe morphological features on the coated and uncoated CVCs. Surface roughness of U—C, BCN-C and $TiO_2$—C was determine using the SPM/AFM dimension 3100 in non-contact tapping mode. Catheter surface area of 100 $\mu m^2$ were scanned for comparison. Separately, random 10 $\mu m^2$ surface scans were obtained to assess peak and valley gradients.

Bacterial Growth on Catheters

Serial dilutions of E. coli K-12 and B. cereus bacterial cultures were made with Luria broth to acquire a cell density of $5 \times 10^4$ cells $ml^{-1}$. Luria broth is used for maintaining and propagating cultures of E. coli and other bacteria for microbiology procedures. One liter of this sterile medium consists of 10 grams of tryptone, 5 grams of yeast, and 10 grams of sodium chloride, with a pH of 7.0.

U—C, BCN-C and $TiO_2$—C segments (1 cm long) were immersed in 5 ml culture in culture tubes with sufficient aeration. Culture tubes were incubated at temperatures of 37° C. and 30° C. for E. coli and B. cereus respectively for 6 h.

Using sterile forceps, catheter segments were removed from culture tubes and rinsed in tubes of sterile water, then rolled onto the surface of nutrient agar plates for E. coli K-12 and blood agar plates for B. cereus (see FIGS. 2a-2f). This technique is known as the roll plate method, and is described in detail in Slobbe et al. 2009 and Mir et al. (2016), herein incorporated by reference in their entirety into this disclosure. (L. Slobbe, A. el Barzouhi, E. Boersma, and B. J. Rijnders, "Comparison of the roll plate method to the sonication method to diagnose catheter colonization and bacteremia in patients with long-term tunneled catheters: a randomized prospective study." J. Clin. Microbiol., 47, 885 (2009); S. V. Nair et al., "Antimicrobial activity of plumbagin, a naturally occurring naphthoquinone from Plumbago rosea, against Staphylococcus aureus and Candida albicans." Int. J. Med. Microbiol., 306, 237 (2016)).

Culture plates were covered and incubated for 24 h at 37° C. and 30° C. for E. coli and B. cereus, respectively. Number of colonies per plate were counted manually and recorded. Experimental values were obtained in triplicates for both E. coli K-12 and B. cereus.

Biofilm Formation and Analysis

Biofilm Growth

Serial dilutions of E. coli K-12 and B. cereus bacterial cultures were made with Luria broth to acquire a cell density of $5 \times 10^6$ cells $ml^{-1}$.

U-C and BCN-C (1 cm long) were immersed in 5 ml culture in culture tubes with sufficient aeration. Culture tubes were incubated at 37° C. for 6 h. All experiments were performed in triplicates.

Catheter segments were removed and rinsed in sterile water. Rinsed catheters were inserted into culture tubes containing 2 ml of Luria broth and incubated at temperatures of 37° C. and 30° C. for E. coli and B. cereus respectively for 24 h.

Staining the Biofilm

Catheter segments were removed and rinsed in sterile water. U—C and BCN-C segments were immersed in tubes containing 0.1% crystal violent solution for 5 min. Crystal violet stained catheter segments were rinsed in sterile water and transferred to separate wells of a 96 well microtiter plate.

Quantifying the Biofilm

125 µl of 30% acetic acid was dripped on to the surface of each catheter, allowing for the adhered biofilm to solubilize into their respective wells. In order to quantify the biofilm, absorbance was performed at 550 nm using SpectraMax iD3 and iD5 multi-mode microplate readers (Molecular Devices). Optical densities of E. coli and B. cereus biofilms on U-C and BCN-C were recorded. 30% acetic acid was used as the blank to record optical density.

Statistical Analysis

The data presented in FIG. 2 is the average of three independent experiments. One tailed student t-test analysis was performed and the probability value (p-value) is reported. Significant difference with p<0.05 are marked with * and highly significant difference with p<0.01 are marked with **.

Example 2—BCN Nano-Coatings Reduce CLABSI Incidence (Prophetic)

Central venous catheters can be coated with BCN to reduce CLABSI. Annually, over 250,000 CLABSIs occur with attributable cause mortality of up to 30%. The most common route of infection is microorganisms on the skin at the catheter insertion site migrating into the catheter tract with colonization of the catheter tip. Additionally, the catheter hub may become contaminated which also leads to intraluminal colonization. While rare, contaminated infusate can also introduce microorganisms into the catheter. Hematogenous spread of infection from another site in the patient can also introduce microorganisms.

The risk of bacterial infection begins as soon as the catheter is inserted. Short term catheters (≤10 days) usually become infected along the outer external surface of the catheter. This colonization is usually the result of migration of microorganisms on the skin at the time of insertion. Catheters placed for longer periods of time (>10 days) usually exhibit intraluminal colonization due to hub contamination. (Wassil, S. K., et al., Antimicrobial impregnated catheters in the prevention of catheter-related bloodstream infection in hospitalized patients, *J Pediatr Pharmacol Ther,* 2007 April-June; 12(2): 77-90).

A 37 year old female patient presents in the hospital in need of a central line. The patient has a history of developing CLABSI in previous hospital visits. A central line catheter that is coated on both its inner and outer surfaces with a BCN nanocoating is inserted into the patient and left in place for 14 days. The catheter surface is coated as described in Example 1. Briefly, RF sputtering is used to coat the catheter surface with a $B_4C$ target with 99.9% purity being used as the source material. The base pressure of deposition chamber is $4\times10^{-7}$ Torr. BCN nano-coatings are deposited at a fixed pressure of 5 mTorr in presence of $N_2/Ar$ (0.25) while maintaining the total gas flow at 20 sccm. RF power to the $B_4C$ target is set at 200 W. The coating on the catheter is about 60-100 nm in thickness with a surface roughness of about 80-120 nm. Upon removal of the catheter, the patient does not present with CLABSI.

Example 3—BCN Nano-Coatings on Sutures Reduces Infection at Wound Site (Prophetic)

Surgical site infection (SSIs) account for at least 20% of all hospital-acquired infections in the U.S and are associated with up to an 11-fold increase in mortality with 77% of the mortality in patients presenting with an SSI is associated with the infection itself. (Vieira, D. et al., Engineering surgical stitches to prevent bacterial infection, *Scientific Reports,* 2022, 12:834). The first antimicrobial surgical suture, approved by the FDA in 2002, was coated with triclosan, however some clinical trials have suggested that such triclosan coatings do not reduce the risk of SSIs. Another alternative antimicrobial coating that has been used is chlorhexidine, which has shown some efficacy in reducing SSIs. (Onesti, M. G. et al., Effectiveness of antimicrobial-coated sutures for the prevention of surgical site infection: a review of the literature, *European Review for Medical and Pharmacological Sciences,* 2018; 22(17): 5729-5739). However, new coatings for inhibiting biofilm formation and bacterial growth are greatly needed.

Two male patients, ages 39 and 45, present with similar leg wounds needing sutures due to a hockey accident. The 39 year old patient's wound is sutured with normal uncoated nylon sutures while the 45 year old patient's wound is sutured with nylon sutures coated with the BCN coating. Sutures are coated with a BCN nano-coating having a thickness of about 80-60-100 nm and a surface roughness of about 80-120 nm. The coating is applied as a film using RF magnetron sputtering at the parameters listed in Example 1. Briefly, RF sputtering is used to coat the suture surface with a $B_4C$ target with 99.9% purity being used as the source material. The base pressure of deposition chamber is $4\times10^{-7}$ Torr. BCN nano-coatings are deposited at a fixed pressure of 5 mTorr in presence of $N_2/Ar$ (0.25) while maintaining the total gas flow at 20 sccm. RF power to the $B_4C$ target is set at 200 W.

Both patients clean the wounds similarly. After a week, the 45 year old patient having the BCN coated sutures exhibits significantly less bacterial growth and infection at the wound site as compared to the 39 year old patient having uncoated sutures.

Example 4—BCN Nano-Coatings on Prosthetic Implants Reduces Infection (Prophetic)

Prosthetic joint infection (PJI) can be a serious complication of joint arthroplasty. PJI generally is an infection between the joint prosthesis and adjacent tissue. The majority of PJIs that occur within 1 year of surgery are caused by the introduction of microorganisms during surgery through direct contact or aerosolized contamination of the prosthesis or periprosthetic tissue. Infection can also be initiated by contiguous spread of infection from an adjacent site.

Biofilm formation has been implicated in PJI which makes treatment difficult, in many cases requiring removal of the prosthesis. Biofilms also make diagnosis of PJI difficult, particularly for delayed and late-onset PJI, as the microorganisms are generally concentrated on the surface of the prosthesis thus limiting the sensitivity of periprosthetic tissue and fluid cultures. (Tande, A. M. and Patel, R., Prosthetic joint infection, *Clinical Microbiology Reviews,* 201 April, 27(2): 302-345).

A 40 year old male patient is admitted for joint replacement in his knee with a metal-to-plastic prosthesis. The prosthesis is coated with a BCN nanocoating having a thickness of about 60-100 nm and a surface roughness of about 80-120 nm. The coating is applied as a film to the surface of the prosthetic using RF magnetron sputtering at the parameters listed in Example 1. Briefly, RF sputtering is used to coat the prosthesis surface with a $B_4C$ target with 99.9% purity being used as the source material. The base pressure of deposition chamber is $4\times10^{-7}$ Torr. BCN nano-coatings are deposited at a fixed pressure of 5 mTorr in presence of $N_2/Ar$ (0.25) while maintaining the total gas flow at 20 sccm. RF power to the $B_4C$ target is set at 200 W. The patient does not ever present with symptoms of PJI or develop PJI.

For comparison, a 35 year old male patient is admitted for knee arthroscopy with a metal-to-plastic prosthesis. The prosthesis is absent any BCN nanocoating. After about 3 months, the patient reports pain in the knee and upon examination, the patient presents with joint swelling and erythema in the affected knee. Testing is performed and a diagnosis of PJI is confirmed.

CONCLUSION

In conclusion, the inventors discovered the inhibitory effects of BCN nano-coatings on bacterial growth and biofilm formation on medical devices such as CVCs. BCN nano-coatings were synthesized using RF sputtering technique. BCN-C reduced bacterial CFUs by 81.14% for *E. coli* and 97.12% for *B. cereus*. $TiO_2$—C was used for comparison and reduced bacterial CFUs by only 19% for both *E. coli* and *B. cereus*. BCN nano-coatings suppressed *E. coli* biofilm formation by 62.13% and *B. cereus* biofilm formation by 75.52%. The bacterial inhibition and antibiofilm ability of BCN-C can be attributed to the surface roughness of CVCs. These observed properties of BCN nano-coating are explored further to reduce catheter and other medical device associated infections.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween. Now that the invention has been described,

What is claimed is:

1. A medical device for subcutaneous disposal at least partially within a patient comprising:

a medical device having at least one polymeric surface having an antimicrobial coating wherein the antimicrobial coating consists of boron carbon nitride (BCN) formed over at least a portion of at least one polymeric surface of the medical device;

wherein the medical device is a catheter and the antimicrobial coating is formed on at least a portion of an inner surface of the catheter, on at least a portion of an outer surface of the catheter, or on at least a portion of both the inner and the outer surfaces of the catheter.

2. The medical device of claim 1, wherein the BCN coating is between about 60-100 nm in thickness.

3. The medical device of claim 1, wherein the BCN coating has an average surface roughness between about 80-120 nm.

* * * * *